US00PP28081P3

(12) United States Plant Patent
Tufaro

(10) Patent No.: US PP28,081 P3
(45) Date of Patent: Jun. 6, 2017

(54) STRAWBERRY PLANT NAMED 'MELISSA'

(50) Latin Name: ***Fragaria×ananassa* Duchesne**
Varietal Denomination: Melissa

(71) Applicant: Nova Siri Genetics S.R.L., Nova Siri (MT) (IT)

(72) Inventor: Nicola Tufaro, Nova Siri (IT)

(73) Assignee: NOVA SIRI GENETICS S. R. L., Nova Siri (MT) (IT)

( * ) Notice: Subject to any disclaimer, the term of this patent is extended or adjusted under 35 U.S.C. 154(b) by 63 days.

(21) Appl. No.: 14/545,597

(22) Filed: May 28, 2015

(65) Prior Publication Data

US 2016/0029528 P1 Jan. 28, 2016

(30) Foreign Application Priority Data

Jul. 23, 2014 (QZ) ..... PBR 2014/1879

(51) Int. Cl.
*A01H 5/08* (2006.01)

(52) U.S. Cl.
USPC ..... Plt./208

(58) Field of Classification Search
USPC ..... Plt./208
See application file for complete search history.

(56) References Cited

PUBLICATIONS

Trademark hit for 'Melissa's Brand'.*

* cited by examiner

*Primary Examiner* — Anne Grunberg
(74) *Attorney, Agent, or Firm* — Buchanan Ingersoll & Rooney PC

(57) ABSTRACT

A new and distinct short-day strawberry plant is provided. Attractive early-ripening substantially uniform medium red primarily conical to slightly rhomboid fruit having a firm flesh is formed in good yield that is longer than broad in configuration. White inflorescence is formed on an early basis that tends to be disposed above the foliage. A calyx commonly is displayed that extends slightly beyond the corolla when open. A semi-dense semi-upright growth habit is displayed.

21 Drawing Sheets

Botanical/commercial classification: *Fragaria×ananassa* Duchesne/Strawberry Plant.

Varietal denomination: cv. Melissa.

BACKGROUND OF THE INVENTION

The new and distinct short-day strawberry plant variety of the present invention was the product of a controlled breeding program that was carried out at Nova Siri (MT) Italy located at 40° 08' 40" N-16° 39' 40" E and 10 meters above sea level. The female parent (i.e., the seed parent) was the 'Siris' cultivar (non-patented in the United States and European Application No. 34843), a strawberry plant variety with medium late-season yield and ability to produce fruits with very high sugar content and presenting a high tolerance to infection by *Pytophthora Cactorum* and *Colletotrichun Acutatum* in plants as well in fruits, and the male parent (i.e., pollen parent) was the 'Margherita' cultivar (U.S. Plant Pat, No. 25,638, filed Jul. 3, 2013 and EU No. 2012/1378), a strawberry variety with high early-season yield, and ability to produce very high yield and very large primary and secondary fruits. The parentage of the new cultivar can be summarized as follows:

'Siris'×'Margherita'.

The seeds resulting from the pollination were sown and small plants were obtained which were physically different from each other. Selective study and testing resulted in the identification of a single plant of the new variety.

The new variety initially was designated 488xf-11-03.

It was found that the new short-day strawberry cultivar of the present invention displays the following combination of characteristics:

(a) exhibits a semi-dense semi-upright growth habit,
(b) displays on an early basis white inflorescence at a level generally above the foliage,
(c) commonly displays a calyx that is slightly larger than the diameter of the corolla when open,
(d) forms in abundance attractive early-ripening large medium red primarily conical to slightly rhomboid fruit having firm flesh that is longer than broad in configuration, and
(e) have a high tolerance to infection by *Colletotricum acutatum.*

The new variety of the present invention can be readily distinguished from previously known strawberry cultivars including the 'Sabrosa' cultivar (U.S. Plant Pat. No. 16,558) as indicated in detail hereafter. The comparative 'Sabrosa' plants described herein were obtained commercially in Italy.

The new variety possesses characteristics that commonly are sought by commercial strawberry growers. The substantially uniform attractive firm medium red early-ripening fruit is provided in good yields. Accordingly, the new cultivar is considered to be a promising new plant for commercial introduction.

The new variety requires an induction period for flowering. This can be achieved by growing in a colder climate away from the equator or at a higher altitude above sea level.

During observation to date no particular disease sensitivity for the new cultivar has been observed.

The new variety has been asexually reproduced by the use of stolons at Ochla, Poland located at 51° 848 N-15° 447 E and at Nova Siri (MT) Italy, and by in vitro tissue culture. No rooting problems were encountered. The combination of characteristics exhibited by the new plant has been found to be stable and is reliably transmitted to succeeding generations following such asexual reproduction. Accordingly, the new variety reproduces true-to-type manner by such asexual reproduction.

The new plant variety has been named 'Melissa'.

BRIEF DESCRIPTION OF THE PHOTOGRAPHS

The accompanying photographs show, as nearly true as it is reasonably possible to make the same in color illustrations of this character, typical specimens of the new cultivar as well as typical specimens of the varieties 'Sabrosa' (U.S. Plant Pat. No. 16,558), 'Siris' (non-patented in the United States and European Application No. 34843), and 'Margherita' (U.S. Plant Pat. No. 25,638, filed Jul. 3, 2013 and EU No. 2012/1378) for comparative purposes. The plants had been asexually reproduced from stolons and were planted under the cover of plastic tunnels during mid-October 2013 at Nova Siri (MT), Italy.

Figure 11:
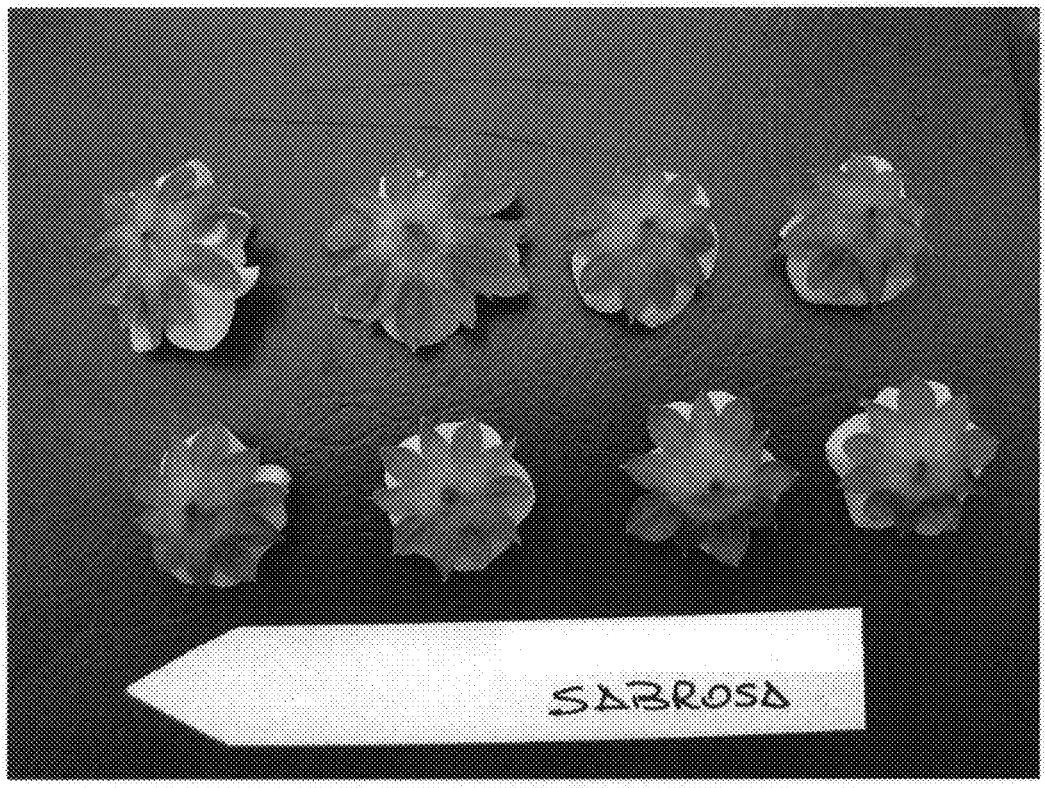

FIG. 11 shows from below for comparative purposes typical flowers of the 'Sabrosa' variety (U.S. Plant Pat. No. 16,558). Unlike the new variety, it is observed that the depicted open calyx commonly is of approximately the same diameter as the open corolla.

Figure 12:
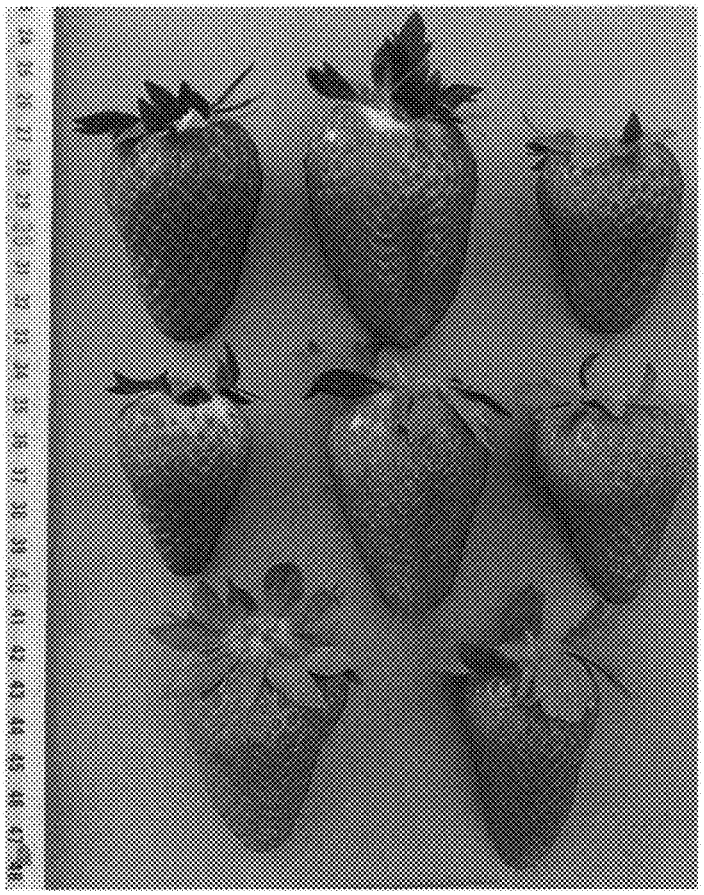

FIG. 12 shows typical large whole medium red fruits of the new variety. Dimensions in centimeters are included at the left for comparative purposes.

Figure 13:
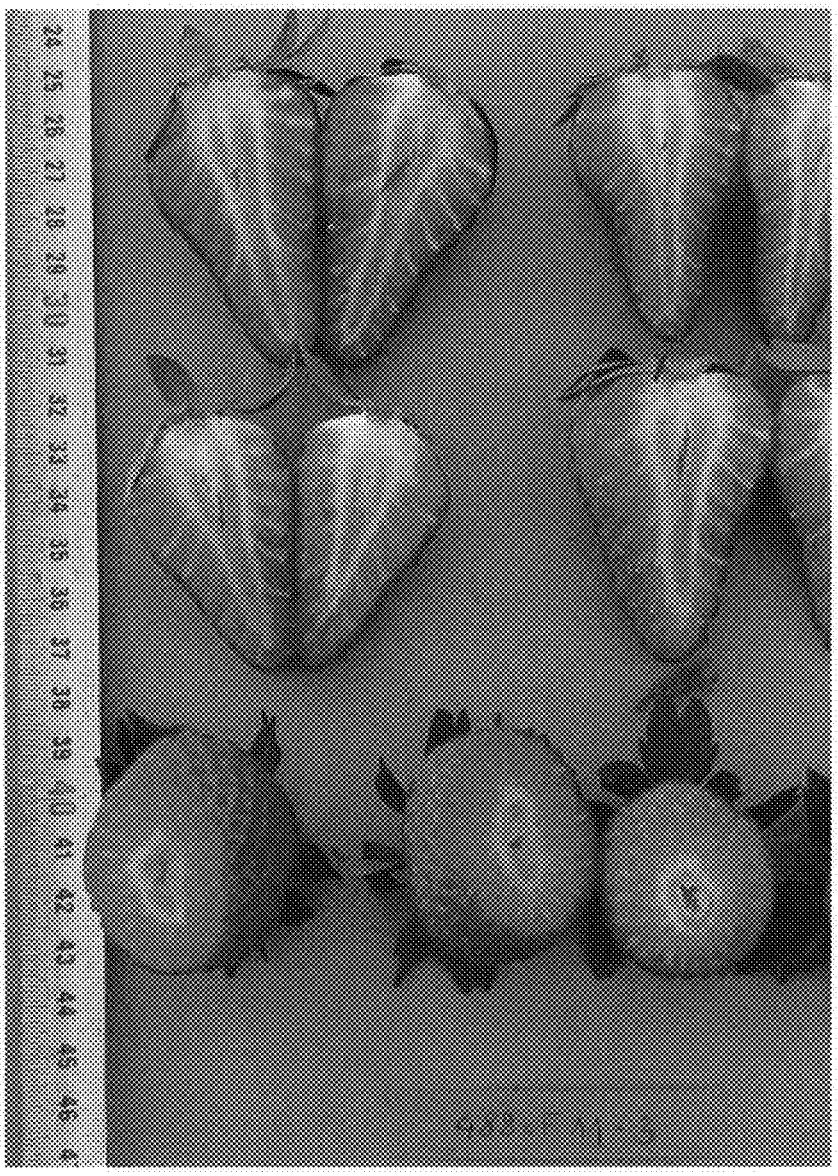

FIG. 13 shows typical internal sections of typical fruits of the new variety. The fruit cavity is shown to be very small or absent. Dimensions in centimeters are included at the left for comparative purposes.

Figure 14:
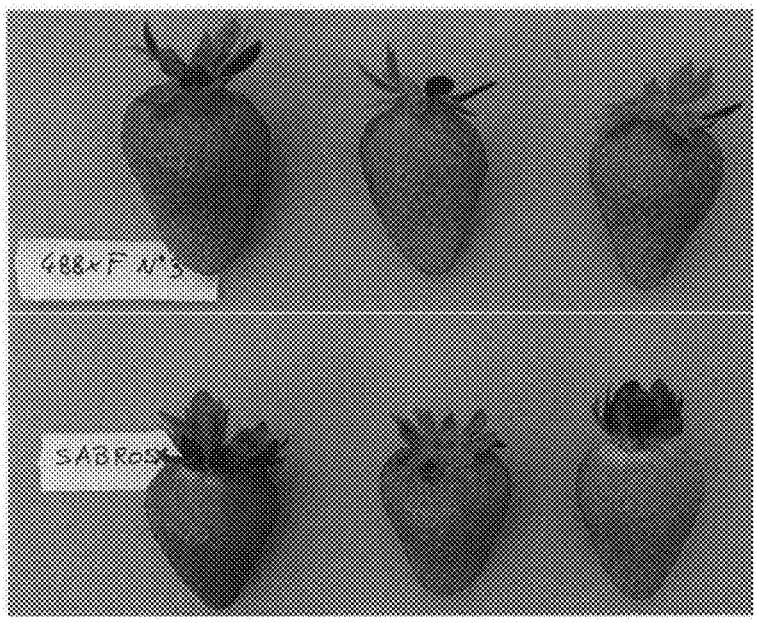

FIG. 14 shows for comparative purposes typical whole fruits of the new variety at the top row and typical whole fruits of the 'Sabrosa' variety (U.S. Plant Pat. No. 16,558) at the bottom row. It will be noted for the new cultivar that the fruits tend to be slightly larger, the calyx is attached at approximately the same level as the fruit surface and substantially without insertion, and the sepal disposition tends to be more outwards rather than upwards.

Figure 2:
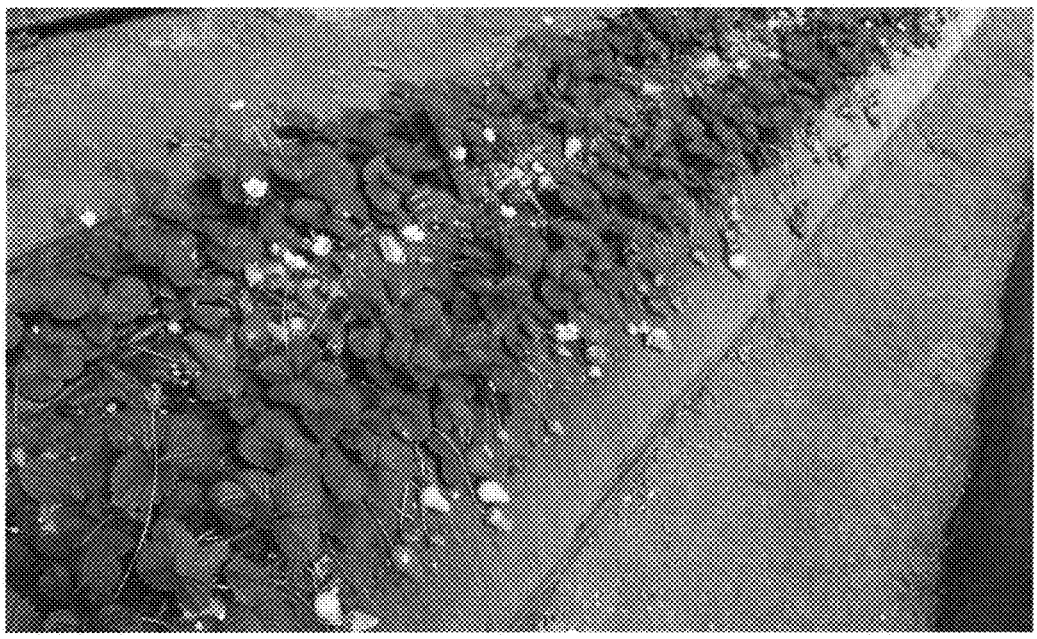
FIG. 2 shows a row of fruiting plants of the new cultivar on Mar. 20, 2014 wherein abundant early fruit production is apparent.
Figure 15:
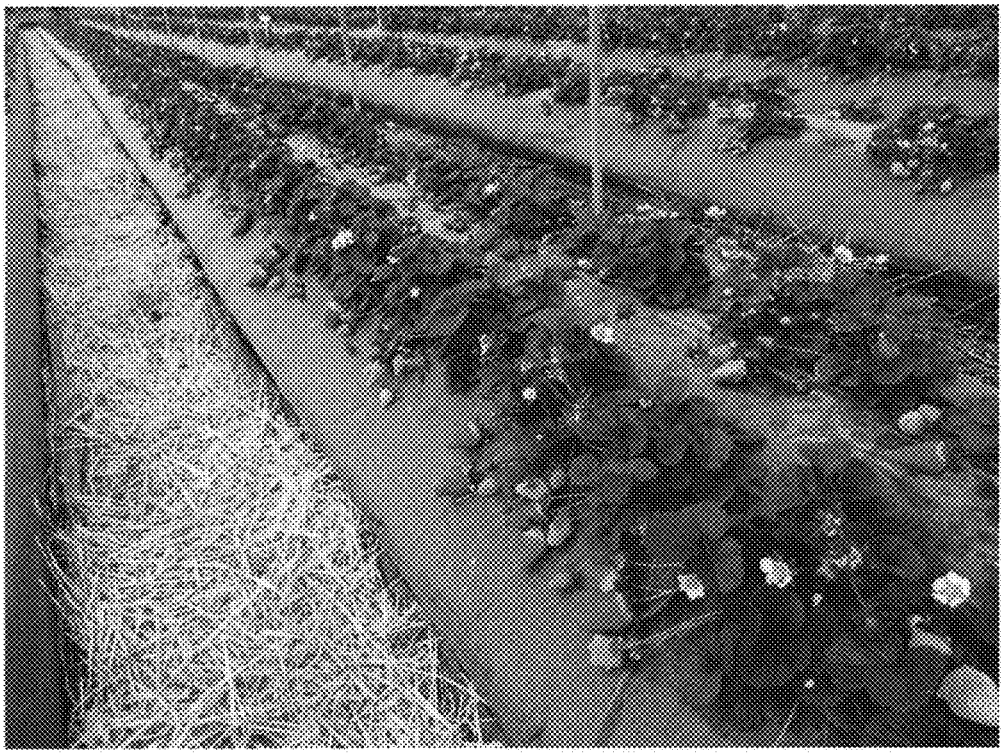

FIG. 15 shows for comparative purposes a row of typical later fruiting plants of the 'Sabrosa' variety (U.S. Plant Pat. No. 16,558) on Mar. 15, 2014. This can be compared with fruiting plants of the new variety of FIG. 2 shown on Mar. 20, 2015. The new variety is shown to display longer peduncles.

Figure 1:
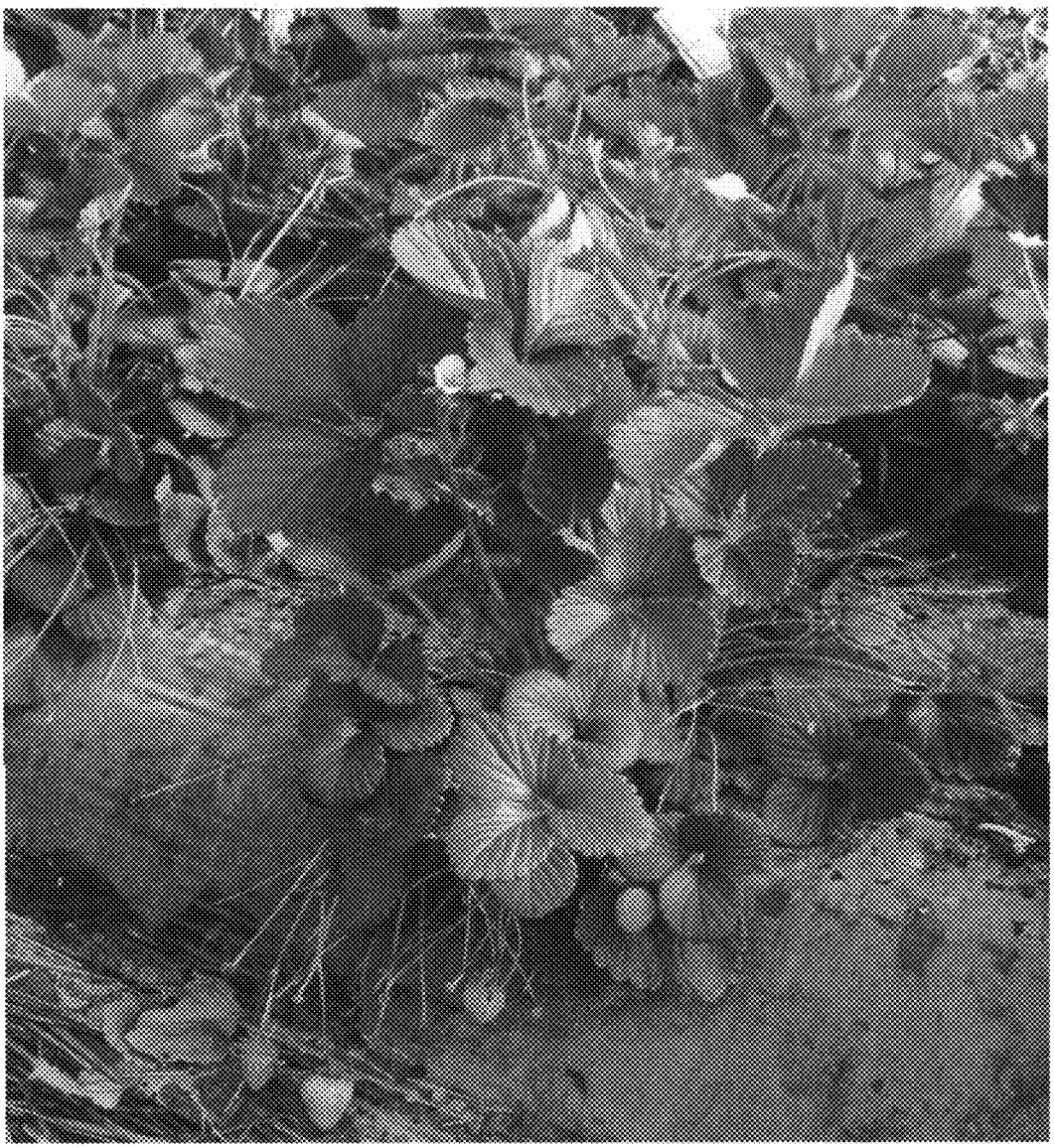
FIG. 1 shows a semi-upright flowering plant of the new variety on May 20, 2014 where the newly formed flowers commonly are disposed above the foliage.
Figure 3:
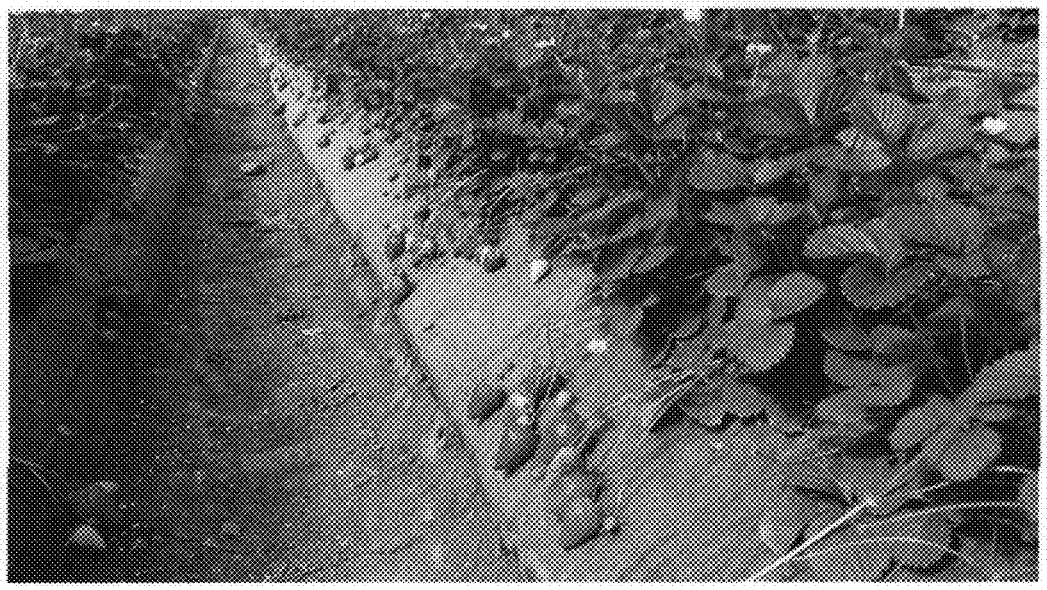
FIG. 3 shows a row of fruiting plants of the new variety on Apr. 30, 2014 wherein vigorous vegetation, newly formed flowers, generally uniform fruit, and very long peduncles are apparent.
Figure 4:
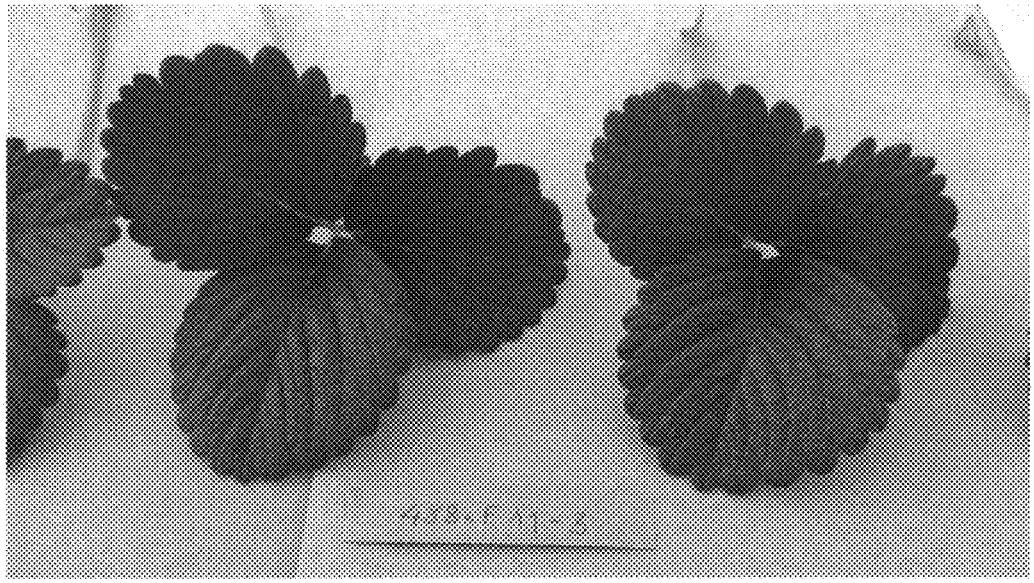
FIG. 4 shows the upper surfaces of two typical three-leaflet leaves of the new variety.
Figure 5:
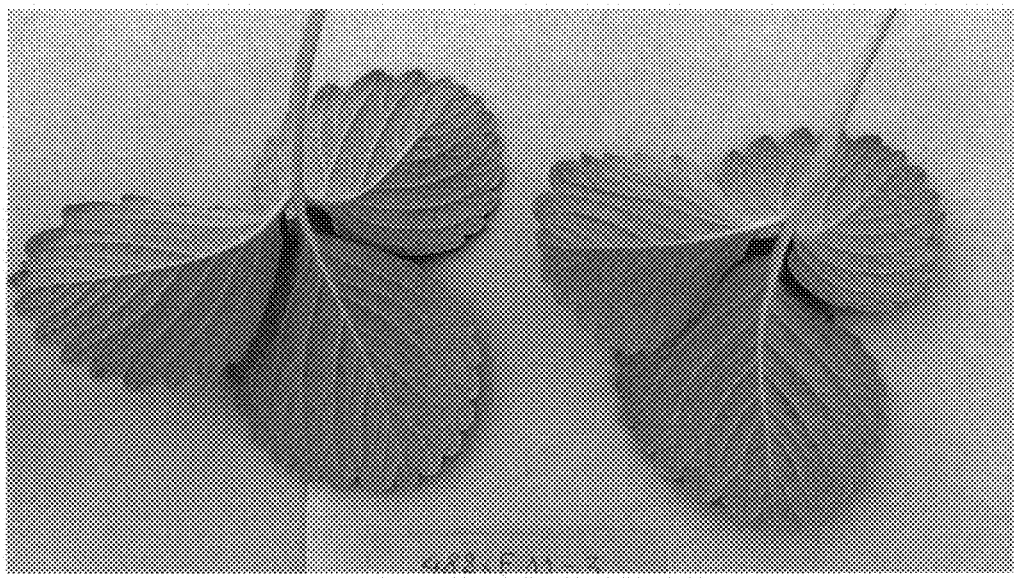
FIG. 5 shows the under surfaces of two typical three-leaflet leaves of the new variety.
Figure 6:
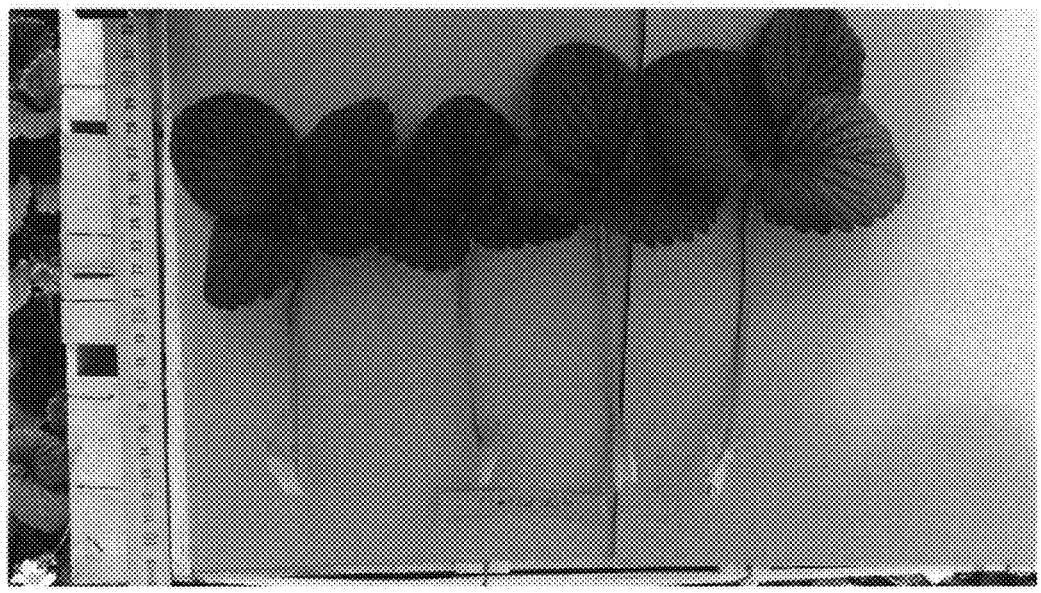
FIG. 6 shows the upper surfaces of four typical three-leaflet leaves of the new variety wherein the petioles and stipules are further apparent. Dimensions in centimeters are included at the left for comparative purposes.
Figure 7:
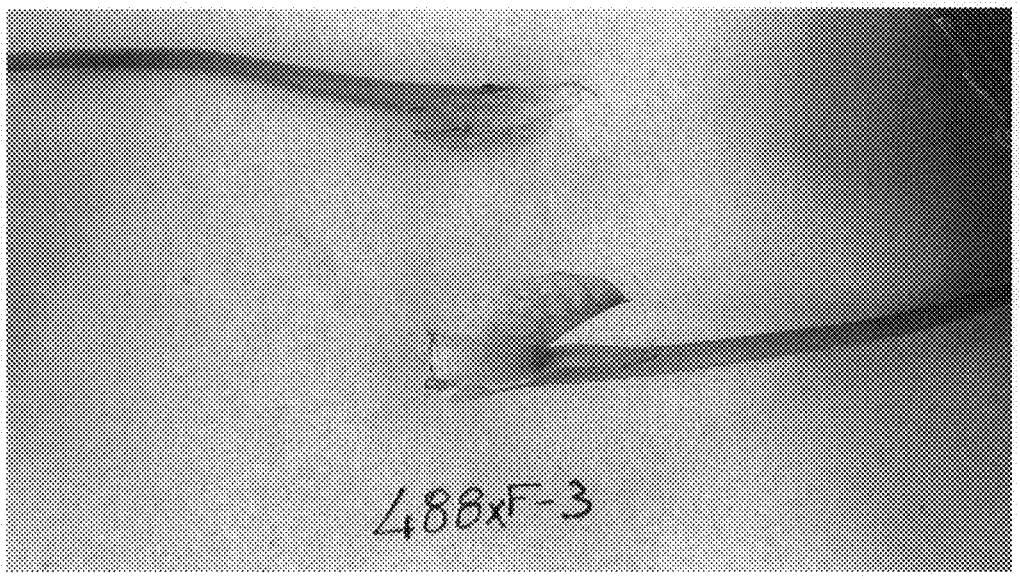
FIG. 7 shows a further close view of typical petioles and stipules of the new variety.
Figure 8:
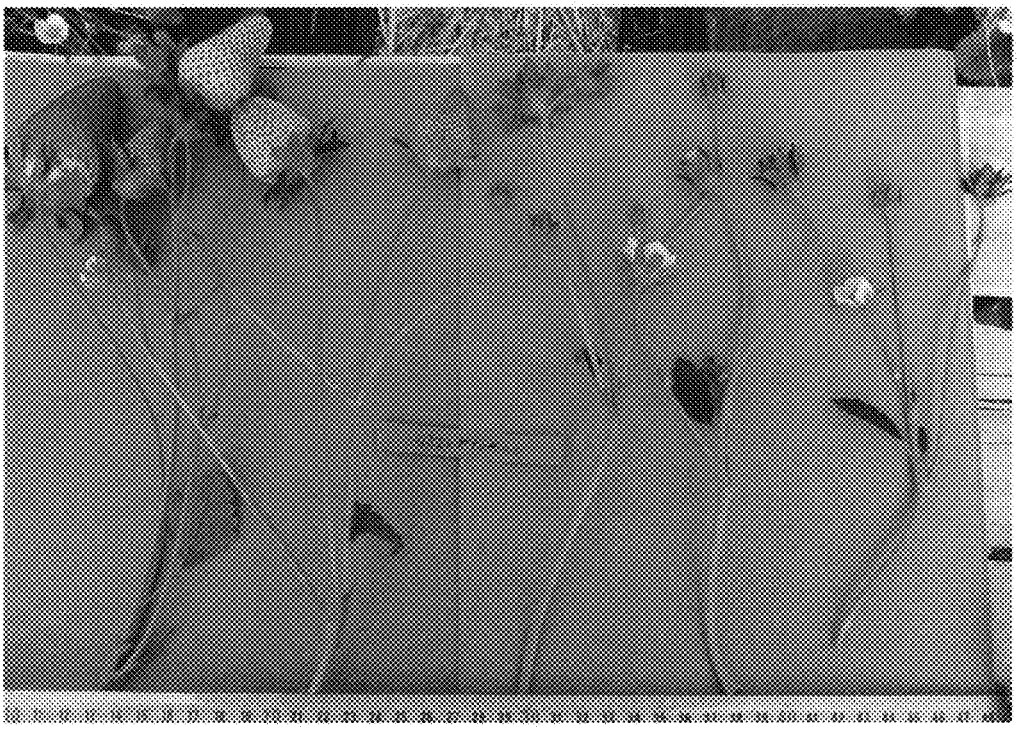
FIG. 8 shows typical inflorescence of the new cultivar as borne on pedicels including the presence of a commonly formed single leaflet. Dimensions in centimeters are included at the bottom for comparative purposes.
Figure 16:
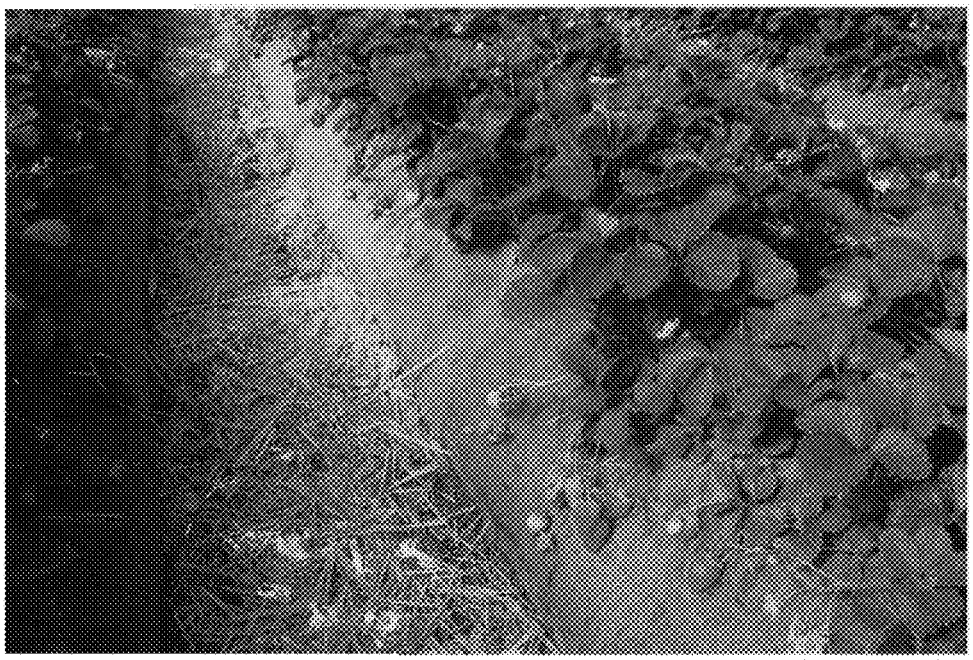

FIG. 16 shows on Apr. 30, 2015 for comparative purposes a row of typical flowering fruiting plants of the 'Sabrosa' variety (U.S. Plant Pat. No. 16,558) where the level of the flowers tends to be at approximately the same as that of the foliage. This can be compared with the typical higher flower level of the new variety as depicted in FIGS. 1, 2, and 3.

Figure 17:
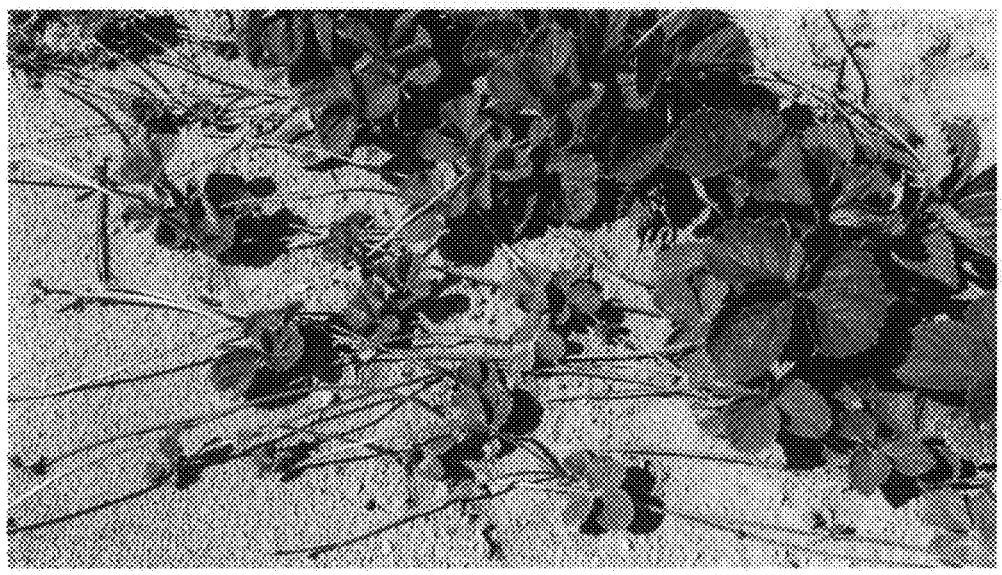

FIG. 17 shows on Jun. 30, 2014 typical long high quality stolons of the new variety which typically are present in medium-to-high quantity with strong anthocyanin coloration.

Figure 18:
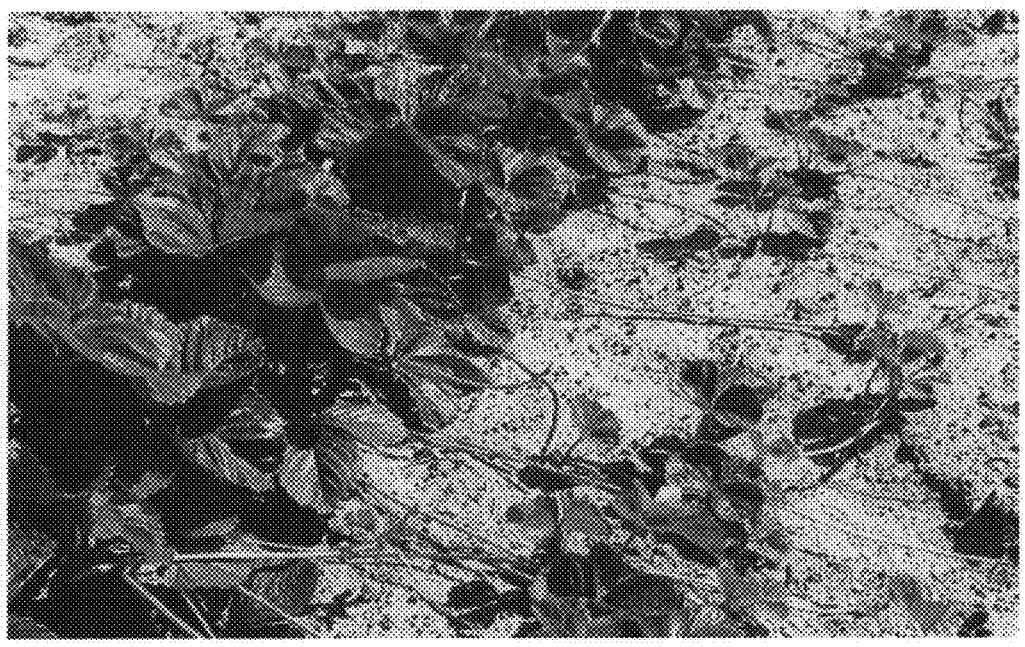

FIG. 18 shows on Jun. 30, 2014 for comparative purposed typical stolons of the 'Sabrosa' variety (U.S. Plant Pat. No. 16,558) which typically are present in low-to-medium quantity with little to weak anthocyanin coloration. This can be compared with FIG. 17 for the typical stolon presentation of the new variety.

Figure 19:
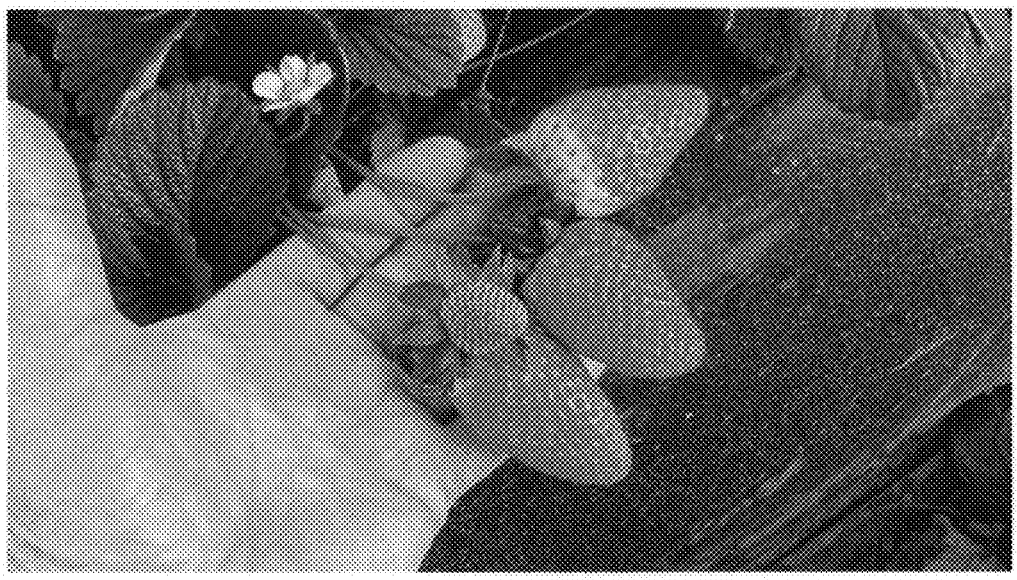

FIG. 19 shows a bouquet of fruits of the new variety and illustrates the small difference between the size of the primary and secondary fruit. Most of the inflorescences of the plants of the new variety have only one flower at the beginning of the season, and at the end of the season the number of flowers increases to approximately 1 to 5 per inflorescence. The size of fruits in new variety is very uniform during with an average weight of 25.87 grams.

Figure 20:
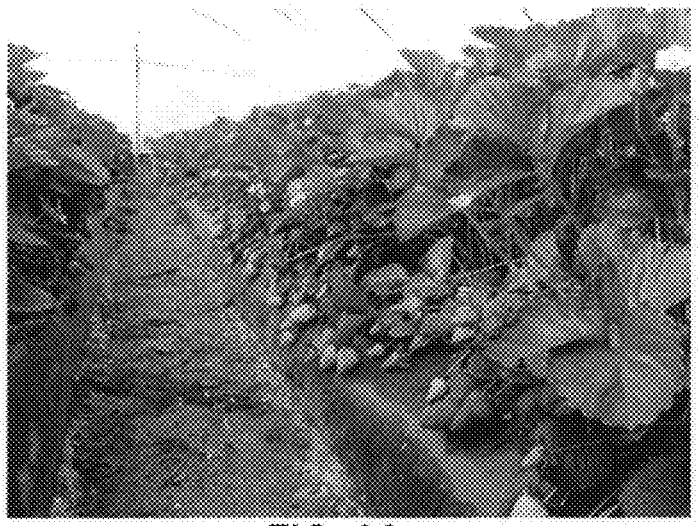

FIG. 20 shows for comparative purposes a row of plants of the 'Margherita' variety (male parent of new variety) (U.S. Plant Pat. No. 25,638) in which it can be seen that the floral peduncles are at the same level as the leaves. In FIG. 1 it can be observed that the flower stalk of the new variety is above the level of the leaves.

Figure 21:
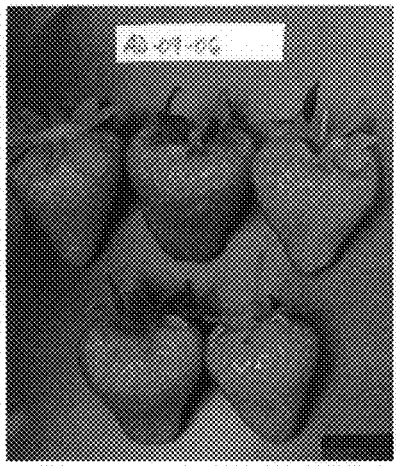

FIG. 21 shows, for comparative purposes fruits from plants of the 'Margherita' variety (male parent of new variety) (U.S. Plant Patent No. 25,638) with a uniform external color, commonly near Red Group 40 to Red Group 44B, and a generally conical shape approximately as long as they are borad and substantially uniform in shape. In FIG. 12 it can be seen that the external color of the fruits of the new variety is substantially uniform medium red, commonly near Red group 45B to Red Group 46 B, and a shape that is conical to slightly rhomboid, longer than they are wide.

Figure 22:
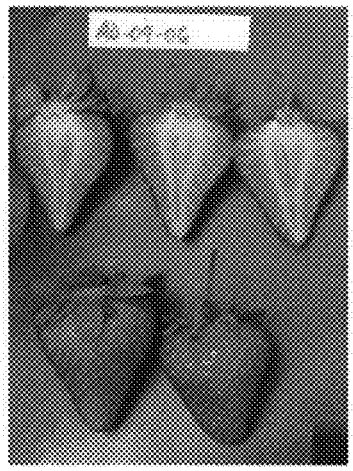

FIG. 22 shows for comparative purposes a cross section of the fruit of plants of the 'Margherita' variety (male parent of new variety) (U.S. Plant Pat. No. 25,638). FIG. 13 shows for comparative purposes a cross section of fruits of the new variety.

Figure 9:
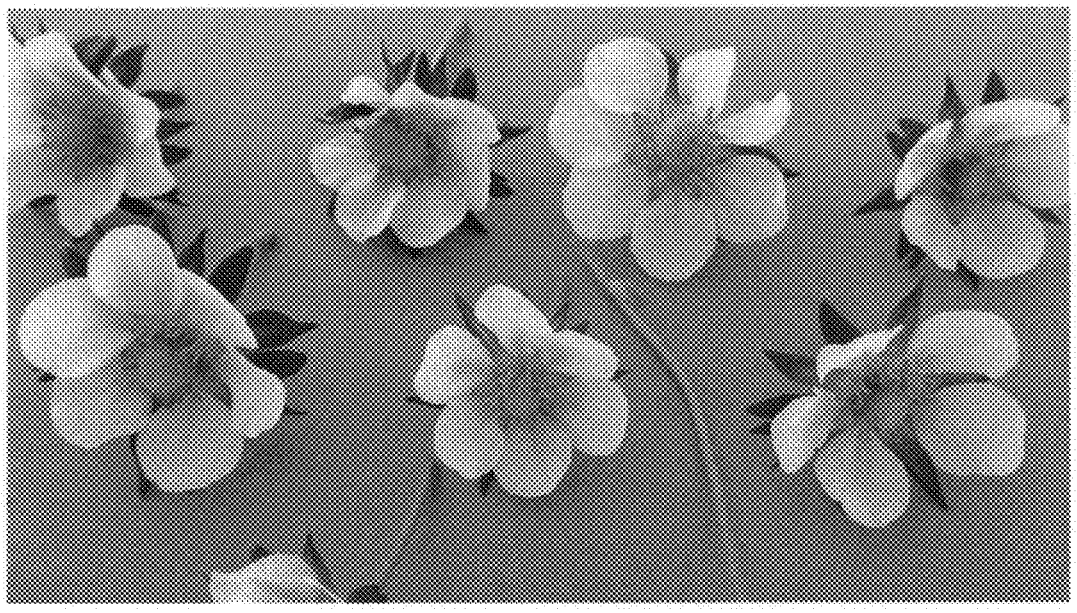
FIG. 9 shows from above a close view of typical flowers of the new variety. The calyx tends to extend somewhat beyond the petals when open.
Figure 10:
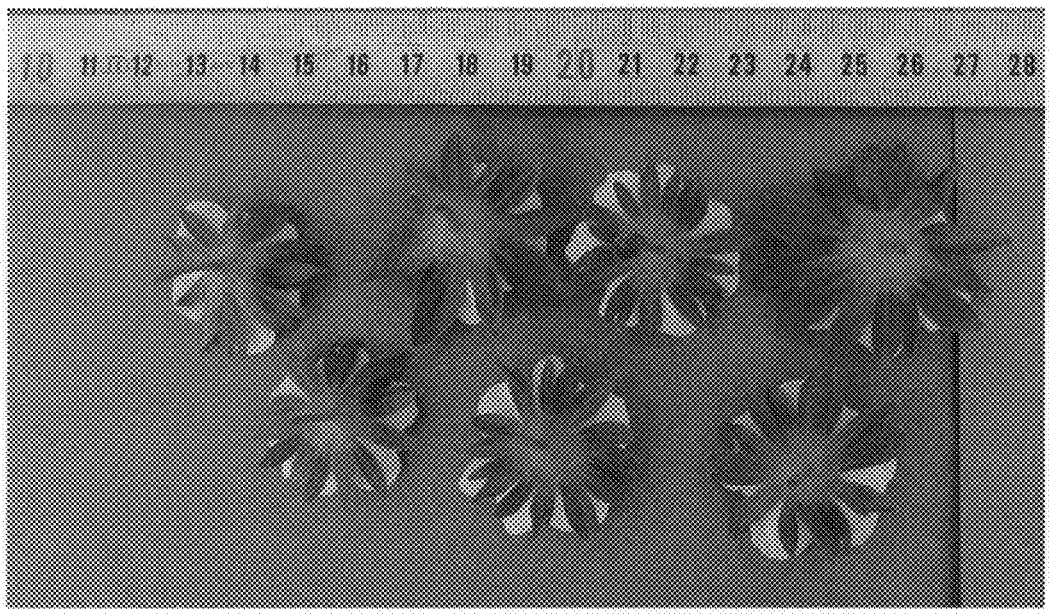
FIG. 10 shows from below a close view of typical flowers of the new variety. Dimensions in centimeters are included at the top for comparative purposes.
Figure 23:
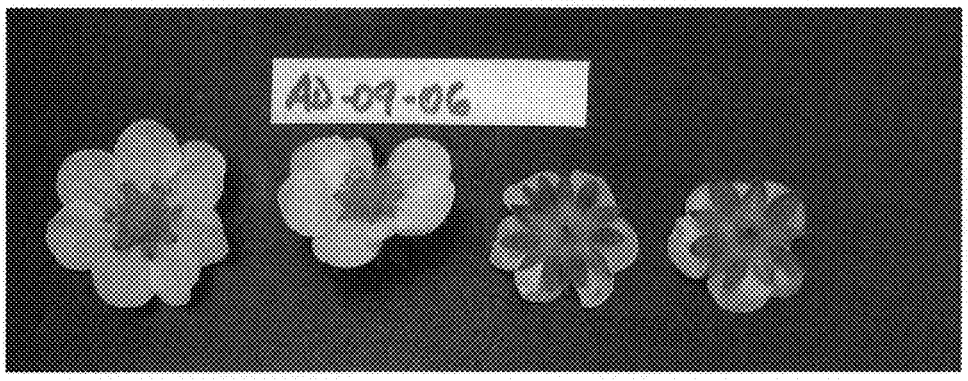

FIG. 23 Shows for comparative purposes flowers of plants of the 'Margherita' variety (male parent of new variety) (U.S. Plant Pat. No. 25,638) which illustrate that the diameter of the corolla is larger than the diameter of calyx. FIGS. 9-10 show flowers of the new variety in which it can be see that the diameter of the calyx is larger than the diameter of the corolla.

Figure 24:
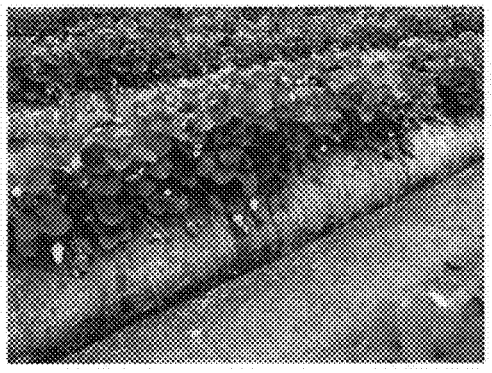

FIG. 24 shows for comparative purposes a typical row of plants of the 'Siris' (designated in the image as "AA 07 488") variety (female parent of new variety) (European Application No 34843) in which it can be seen that the floral peduncles are approximately level with the leaves. In FIG. 1 it can be seen that the new variety provides a semi-upright flowering plant, where the newly formed flowers commonly are disposed above the foliage.

Figure 25:
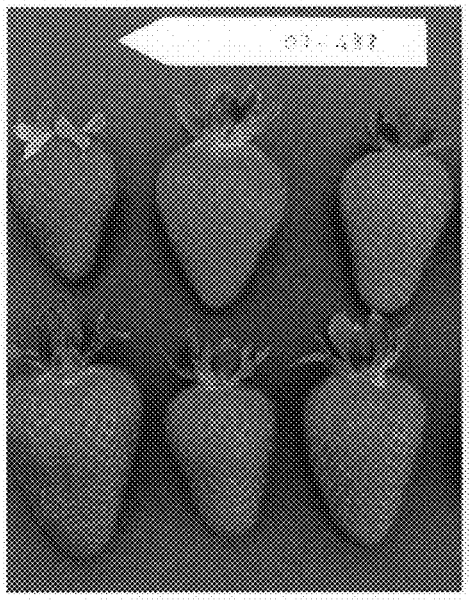

FIG. 25 shows for comparative purposes fruits from plants of the 'Siris' (designated in the image as "AA 07 488") variety (female parent of new variety) (European Application No 34843) with a uniform external color, commonly near Red Group 43A to Red Group 44A, with a generally conical shape, longer than broad, and substantially uniform. In FIG. 12 it can be seen that fruits from plants of the new variety have an external color that is substantially uniform medium red, commonly near Red group 45B to Red Group 46 B, with a generally conical to slightly rhomboid shape, longer than they are broad. The position of the sepals in fruits of the 'Siris' variety is upwards and slightly raised, whereas in the fruits of the new variety the sepals are outwards.

Figure 26:
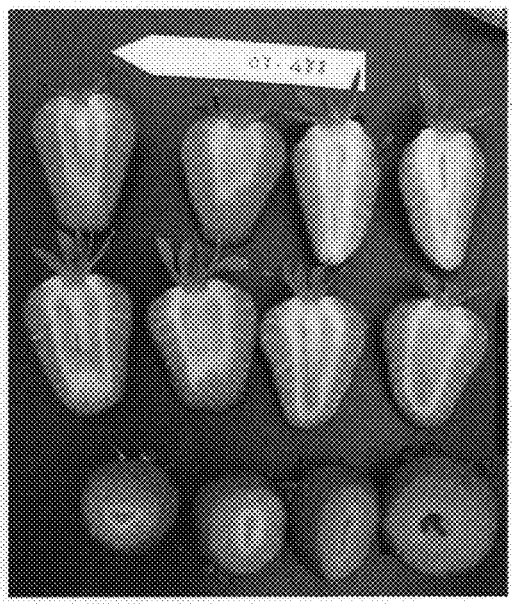

FIG. 26 shows for comparative purposes a cross section of the fruit of the 'Siris' variety (female parent of new variety) (European Application No 34843) in which the flesh internal color is medium red, commonly near Orange Red Group 33A to Orange Red group 33B, with a core that is unevenly colored, commonly near Orange Group 27A to Orange Group 28A. FIG. 13 shows for comparative purposes a cross section of fruits of the new variety in which the flesh internal color is medium red, commonly near Orange-Red Group 34A to Orange Red Group 34B, and the core commonly is medium Orange-Red Group 34A to Orange-Red Group 34B.

Figure 27:
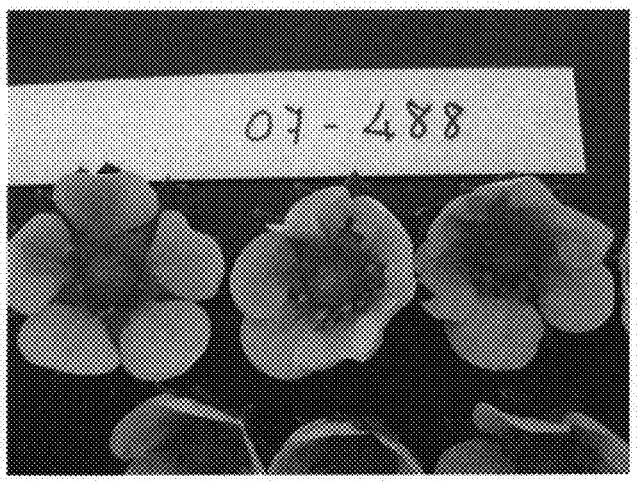

FIG. 27 shows for comparative purposes flowers of plants of the 'Siris' variety (female parent of new variety) (European Application No 34843) where it can be observed that the diameter of the corolla is larger than the diameter of calyx. FIGS. 9-10 show flowers of plants of the new variety in which it can see that the diameter of the calyx is larger than the diameter of the corolla.

DETAILED BOTANICAL DESCRIPTION

The described plants had been asexually reproduced by the use of stolons and were growing under the cover of plastic tunnels at Nova Siri (MT) Italy and at Ochla, Poland. The chart used in the identification of color is The R.H.S. Colour Chart (Edition V) of The Royal Horticultural Society, London, England. Reference to common color terms is to be accorded ordinary dictionary significance.

Botanical class: *Fragaria×ananassa*, Duchesne, cv. 'Melissa'.

Plant:

*Type*.—Short-day.

*Configuration*.—Semi-upright and semi-dense.

*Vigor*.—Strong.

*Leaflets*.—Medium in size, commonly three in number, approximately 6.5 cm in length on average and approximately 6 cm in width on average; the terminal leaflet commonly is moderately longer to equal in length than width, possesses a generally flat cross-section, possesses a serrate to crenate margin, and an acute base; blistering commonly is medium in quantity; the glossiness on the upper surface is medium; and variegated coloration commonly is absent with the upper surface coloration commonly being near Green Group N137C to Green Group N137D and the under surface commonly being near Yellow-Green Group 147B. Such coloration commonly is darker than that of the 'Sabrosa' variety.

*Stolons*.—Numerous in quantity, medium pubescence in density, commonly near Red-Purple Group 67A to Red-Purple Group 67B in coloration, commonly are produced somewhat more numerously than the 'Sabrosa' variety with anthocyanin coloration commonly being weak to absent on the stolons of the 'Sabrosa' variety. The coloration of stolons for the 'Sabrosa' variety commonly is near Yellow-Green Group N144A to Yellow-Green Group 145C.

*Petioles*.—Commonly approximately 10 to 22 cm in length on average, near Yellow-Green Group N144B in coloration, and commonly bear generally horizontally disposed fine pubescence.

*Stipules*.—Commonly approximately 2 to 3 cm in length, and commonly bear some weak anthocyanin coloration of near Red-Purple Group 73A to 74C.

Inflorescence:

*Flowering time*.—Early.

*Flower disposition*.—Generally above the foliage.

*Flower number*.—Medium, commonly 3 to 7.

*Pedicel hairs*.—Pubescence generally disposed somewhat upwards.

*Pedicel color*.—Near Yellow-Green Group 144C to Yellow-Green Group 144B.

*Size*.—Large, with primary flowers commonly being approximately 2.2 to 3.2 cm in diameter on average, and secondary flowers commonly being approximately 2.1 to 2.5 cm in diameter on average, commonly the open calyx is slightly larger than the diameter than the corolla.

*Petals*.—Overlapping, commonly number approximately 5 to 7 on average (typically 6), somewhat rounded overall in configuration with the relationship of the length to the width being substantially equal, commonly approximately 13 mm on average in length and width, and with a rounded apex, and near White Group N155A in coloration on the upper surface.

*Anthers*.—Commonly number approximately 20 to 32 on average, commonly disposed below the stamen, and near Yellow Group 6D to 7D in coloration. The new cultivar is self-fertile and pollen is formed in abundance.

*Sepals*.—Generally lanceolate in configuration, generally somewhat outwardly disposed, commonly number approximately 12 to 14 on average which can be compared to approximately 10 to 12 on average for the 'Sabrosa' cultivar, commonly approximately 1 to 1.7 cm in length on average and approximately 2 to 6 mm in width on average at the broadest point, unlike the 'Sabrosa' cultivar the diameter of the open calyx commonly is slightly greater than that of the corolla (as illustrated in FIGS. 10 and 11), and the coloration on the upper surface is commonly near Green Group 141B to Green Group 143A and on the lower surface is commonly near Yellow-Green Group 147B.

Fruit:

*Bearing*.—Non-remontant.

*Timing*.—Early-fruiting commonly with approximately 30 to 35 days from first blooming to first fruit ripening. This can be compared to approximately 35 to 40 days between first blooming and first fruit ripening for the 'Sabrosa' variety.

*Shape*.—Conical to slightly rhomboid, longer than broad, commonly with a medium difference between terminal and other fruit.

*Size*.—Large, with the primary fruit commonly being approximately 6.5 to 7 cm in length on average and approximately 4 to 4.9 cm in width on average at the broadest point.

*Surface*.—Slightly uneven texture with strong glossiness.

*External color*.—Substantially uniform medium red and commonly near Red Group 45B to Red Group 46B in coloration.

*Internal color*.—Flesh is medium red, and commonly near Orange-Red Group 34A to Orange-Red Group 34B, and the core commonly is medium red Orange-Red Group 34A to Orange-Red Group 34B.

*Firmness*.—Good firmness.

*Cavity*.—Very small or absent fruit cavity (as illustrated in FIG. 13).

*Achenes*.—Located generally below the fruit surface and cover nearly the entire fruit surface commonly with only a very narrow band (if any) where achenes are absent, and commonly near Orange Group 28A to Red Group 45B in coloration.

*Calyx*.—Commonly the fruit is slightly raised at the point of attachment, the calyx commonly attaches to the fruit with medium adherence, the sepals are disposed generally outwards, and the fruit diameter and the calyx diameter commonly are substantially equal.

*Peduncle*.—Very long, commonly approximately 25 to 35 cm in length on average for primary fruit, and commonly near Green Group 141B to Green Group 143A in coloration.

*Pedicel*.—Commonly with pubescence extending upwards, and near Yellow-Green Group 144C to Yellow-Green Group 144B in coloration.

SUPPLEMENTAL COMPARATIVE DATA

Hereafter, additional comparative fruit data is provided for the new 'Melissa' variety and the 'Sabrosa' variety. The plants had been asexually reproduced by the use of stolons and were growing under the cover of plastic tunnels. The fruit was evaluated and compared on the dates indicated. Average data is presented.

Accumulated Production of First Quality Fruit (g/plant)

| Cultivar | February 30th | March 30th | April 30th | May 30th |
|---|---|---|---|---|
| 'Melissa' | 78 | 258 | 362 | 496 |
| 'Sabrosa' | 24 | 119 | 237 | 389 |

Overall Comparison of Average Fruit Weight

| Cultivar | g/fruit |
|---|---|
| 'Melissa' | 26.28 |
| 'Sabrosa' | 22.75 |
| 'Margherita' | 30.45 |
| 'Siris' | 21.50 |

Average Fruit Weight on Specified Dates

| Cultivar | March 30th (grams) | April 30th (grams) | May 30th (grams) |
|---|---|---|---|
| 'Melissa' | 27.88 | 26.75 | 23.00 |
| 'Sabrosa' | 24.43 | 21.00 | 20.40 |
| 'Margherita' | 31.40 | 30.50 | 29.45 |
| 'Siris' | 23.75 | 20.50 | 20.00 |

Fruit Analysis

| | 'Melissa' | 'Sabrosa' | 'Margherita' | 'Siris' |
|---|---|---|---|---|
| Firmness (average)* | 0.74 | 0.74 | 0.60 | 0.80 |
| Dry Matter (%)** | 7.15 | 8.95 | 7.80 | 8.50 |
| pH (to 20°) | 3.93 | 3.81 | 3.55 | 3.75 |
| Acidity as Anhydride Citric (%) | 0.60 | 0.88 | 0.75 | 0.80 |
| Soluble Solids (% Brix) | 9.08 | 9.48 | 8.27 | 9.85 |
| Maturity Index*** | 15.13 | 10.77 | 11.02 | 12.31 |

*Resistance to penetration measured in kilograms using a Turoni (Italy) pentrometer (20 Kg × 0.01).
**weight of residue from the titration of the fruit after drying at 103° C. until a constant weight is achieved.
***Relation between soluble solids and acidity as acetic anhydride.

Plants of the new 'Melissa' variety have not been observed under all possible environmental conditions to date. Accordingly, it is possible that the phenotypic expression may vary somewhat with changes in light intensity and duration, cultural practices, and other environmental conditions.

I claim:

1. A new and distinct short-day strawberry plant that exhibits the following combination of characteristics:

(a) exhibits a semi-dense semi-upright growth habit, (b) displays on an early basis white inflorescence at a level generally above the foliage, (c) commonly displays a calyx that is slightly larger than the diameter of the corolla when open, and (d) forms in abundance attractive early-ripening large medium red primarily conical to rhomboid fruit having firm flesh that is longer than broad in configuration;

substantially as illustrated and described.

* * * * *